United States Patent
Chin et al.

[19]

[11] Patent Number: 6,053,863
[45] Date of Patent: *Apr. 25, 2000

[54] PERIVASCULAR SELF-RETAINING RETRACTOR AND METHOD

[76] Inventors: Albert K. Chin, 2021 Newell Rd., Palo Alto, Calif. 94303; Timothy J. McCoy, 2 Cottage La., San Carlos, Calif. 94070-1816; Jonathan L. Podmore, 444-15th Ave., No. 307, San Francisco, Calif. 94118; Joseph J. Nemeth, 713 Orange Ave., Los Altos, Calif. 94022

[ * ] Notice: This patent is subject to a terminal disclaimer.

[21] Appl. No.: 09/141,869

[22] Filed: Aug. 27, 1998

Related U.S. Application Data

[63] Continuation of application No. 08/866,335, May 30, 1997, Pat. No. 5,921,919.

[51] Int. Cl.$^7$ ...................................................... A61B 17/02

[52] U.S. Cl. ........................... 600/217; 600/215; 600/232

[58] Field of Search .................................... 600/201–235; 623/198; 604/104, 105

[56] References Cited

U.S. PATENT DOCUMENTS

| | | |
|---|---|---|
| 5,782,753 | 7/1998 | DeFonzo et al. . |
| 5,921,919 | 7/1999 | Chin et al. ................................ 606/217 |

*Primary Examiner*—Gary Jackson
*Assistant Examiner*—William Lewis
*Attorney, Agent, or Firm*—Fenwick & West LLP

[57] ABSTRACT

Apparatus and method for expanding a perivascular cavity at a surgical site includes an elongated retractor having a tip at the distal end for convenient insertion into a perivascular cavity, and having a slidable coupler near the proximal end for convenient coupling to an elevator element supported in a retractor frame. The elongated retractor supports an endoscope thereon to facilitate visualization of surrounding tissue during insertion into the perivascular cavity. With the retractor inserted in the cavity, the retractor frame is positioned on the skin in alignment with and straddling the cavity, and the elevator element is selectively coupled to the retractor to elevate the retractor relative to the base of the retractor frame, thereby to expand or distend the cavity to provide ample access to tissues and vessels for surgical manipulations within the cavity.

9 Claims, 5 Drawing Sheets

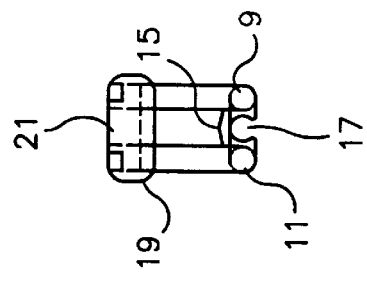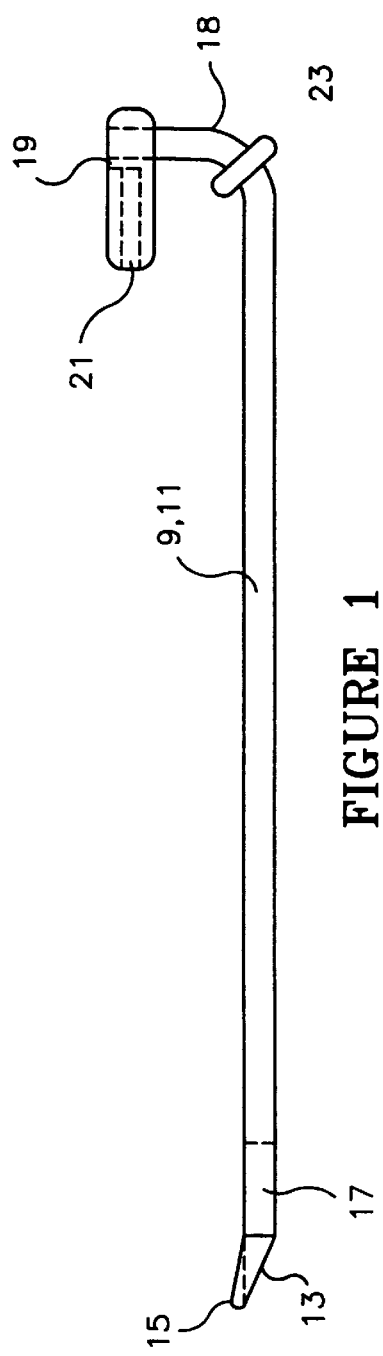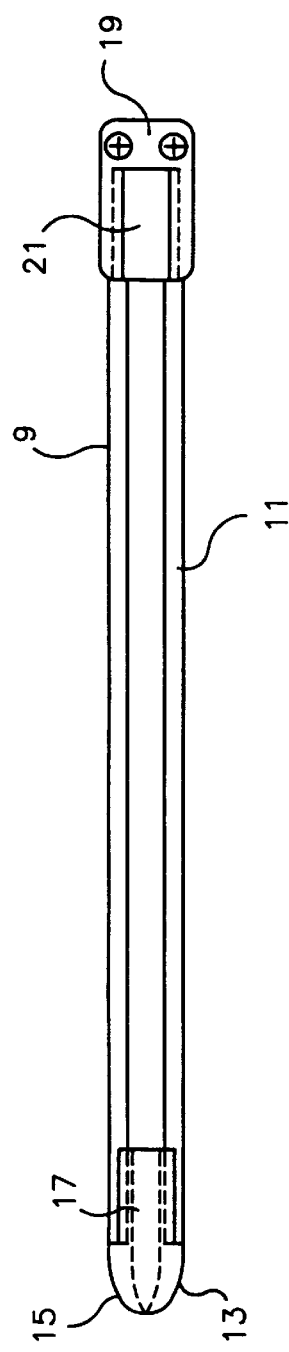

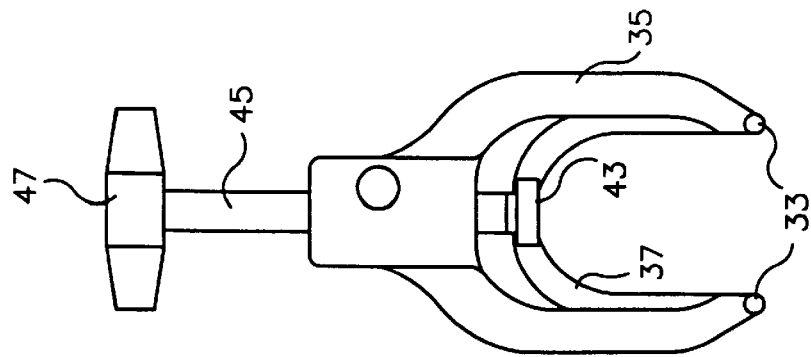
FIGURE 6
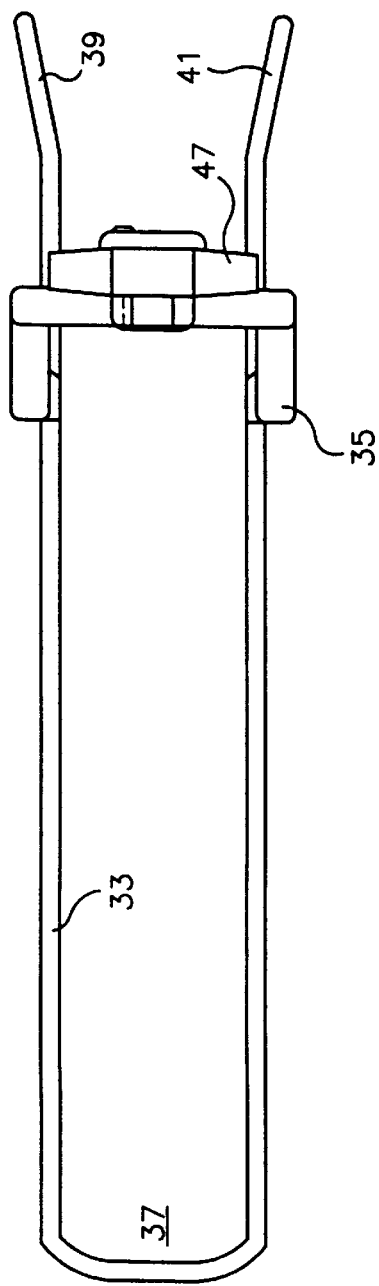
FIGURE 7
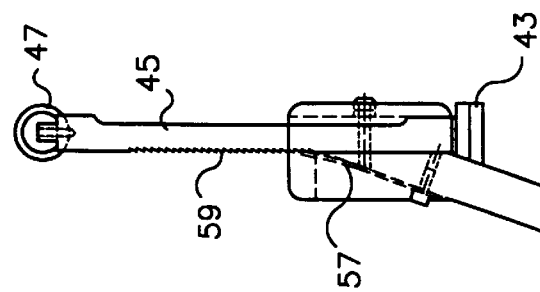
FIGURE 5
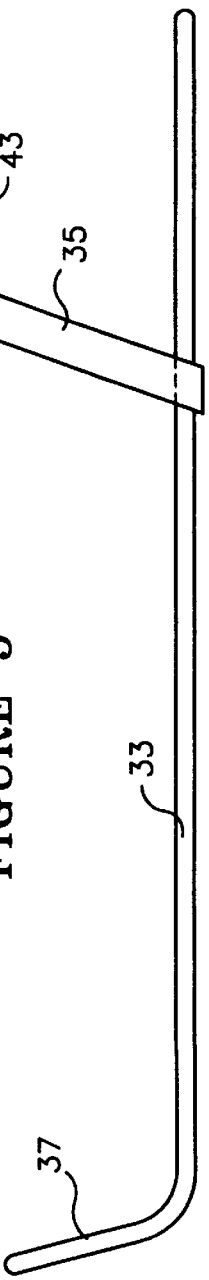

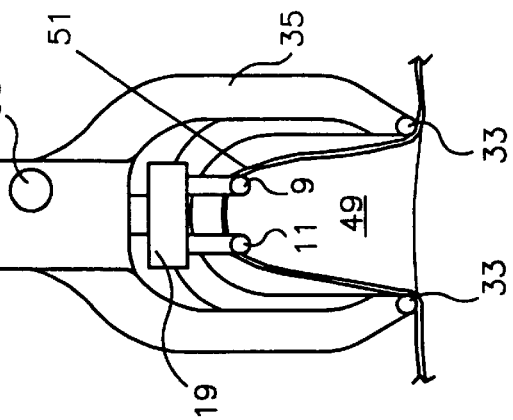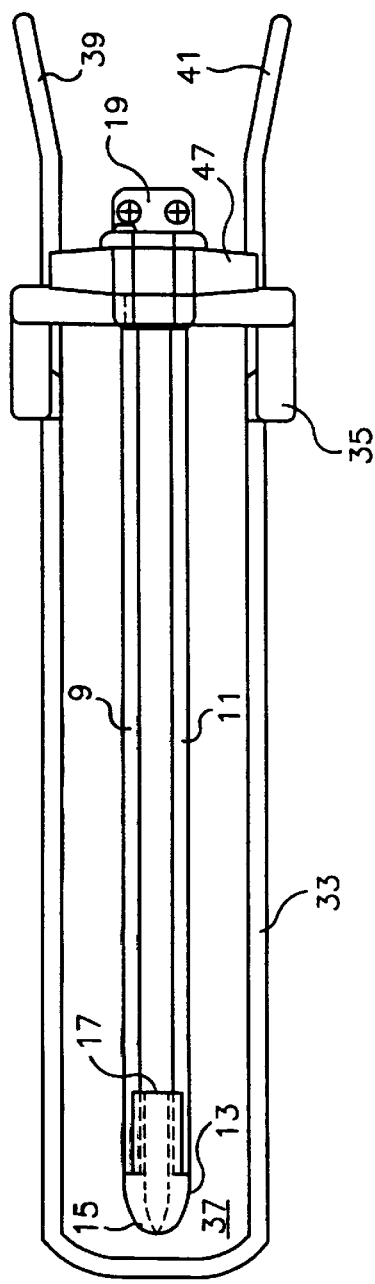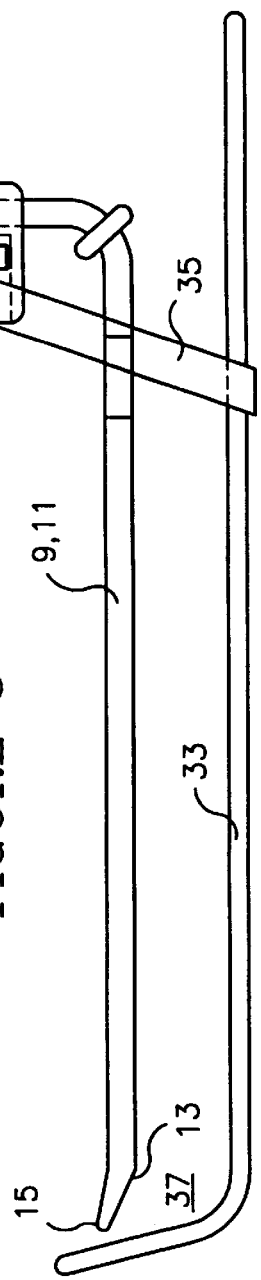

PERIVASCULAR SELF-RETAINING RETRACTOR AND METHOD

This application is a continuation of Ser. No. 08/866,335 filed May 30, 1997 now U.S. Pat. No. 5,921,919.

FIELD OF THE INVENTION

This invention relates to apparatus and method for accessing within a working cavity a vessel to be harvested for use, for example, in coronary artery bypass surgery, and more particularly to a multi-component system and method for facilitating expansion of a working cavity along the course of a vessel of interest.

BACKGROUND OF THE INVENTOR

A perivascular cavity may be formed along the course of a vessel to be harvested using a cannula having a transparent tapered tip. Such devices and procedures dissect tissue planes adjacent the target vessel while visualizing the vessel and connective tissue through the transparent tip via an endoscope within the cannula. Devices and procedures of these types are disclosed in the literature (See, for example, U.S. patent applications Ser. Nos. 08/593,533 now abandoned, and 08/502,494 now abandoned).

Once the perivascular cavity is formed adjacent the target vessel, it is desirable to retain the cavity in expanded condition to facilitate the surgeon's manipulation of connective tissue and lateral or branch vessels in order to liberate, "or harvest", the target vessel from the surgical site. Insufflation of the perivascular cavity using gas such as $CO_2$ under pressure is commonly used to expand the working space within the cavity, but this procedure inhibits relatively free movement of instruments about the vessel of interest within the insufflated cavity due to the requirement for a gas-sealing port into the cavity. In contrast, mechanical retraction mechanisms are known which physically expand at least an entry portion of the cavity to facilitate direct visualization into the cavity, essentially via eye-level alignment with the separated tissue planes at the entry portion of the cavity. Simple traction mechanisms such as a stiff rod inserted into the perivascular cavity to lift up or otherwise retract the surrounding tissue away from the vessel of interest are known to be marginally useful because an additional hand may be occupied keeping adjacent tissue in tension via such retraction rod.

SUMMARY OF THE INVENTION

In accordance with the present invention, a self-retaining retractor and associated fixture allow a surgeon to use both hands freely for surgical manipulation and tissue dissection. An endoscope is held in position along the retractor to facilitate the surgeon's manipulation of two instruments at the same time in contrast to manipulating only one instrument while positioning the endoscope.

In one embodiment, a channeled retractor includes an upturned distal end above a grooved or channeled receptor that receives and supports therein the objective end of an endoscope. The upturned distal end promotes enhanced separation of connective tissue in view of the endoscope as the retractor is advanced into the perivascular cavity adjacent the target vessel. The grooved or channeled receptor receives the tip of an endoscope of, say, 5 mm diameter for clear visualization of tissue distal to the upturned end of the retractor as the retractor is advanced into the perivascular cavity. The channel of the retractor supports a tube which supports the endoscope therein, and such channel may be formed of a pair of stiff rods mounted in parallel spaced orientation, with the supporting tube disposed intermediate the space between rods that form the retractor.

The proximal end of the retractor includes a detachable coupler for convenient attachment to a handle to facilitate initial manual insertion of the retractor into the perivascular cavity, and thereafter for convenient attachment to a retractor frame for maintaining the retractor in elevated position relative to the target vessel.

BRIEF DESCRIPTION OF THE DRAWINGS

FIG. 1 is a side view of the retractor according to one embodiment of the present invention;

FIG. 2 is an end view of the retractor of FIG. 1;

FIG. 3A is a top view of the retractor of FIG. 1;

FIG. 5 is a side view of a retractor frame according to one embodiment;

FIG. 6 is an end view of the retractor frame of FIG. 5;

FIG. 7 is a top view of the retractor frame of FIG. 5;

FIG. 8 is a side view of the retractor of FIG. 1 and the retractor frame of FIG. 5 in assembled configuration;

FIG. 9 is an end view of the assembly of FIG. 8 in operation within and about a perivascular cavity;

FIG. 10 is a top view of the assembly of FIG. 8;

DETAILED DESCRIPTION OF THE INVENTION

Figure 3B:
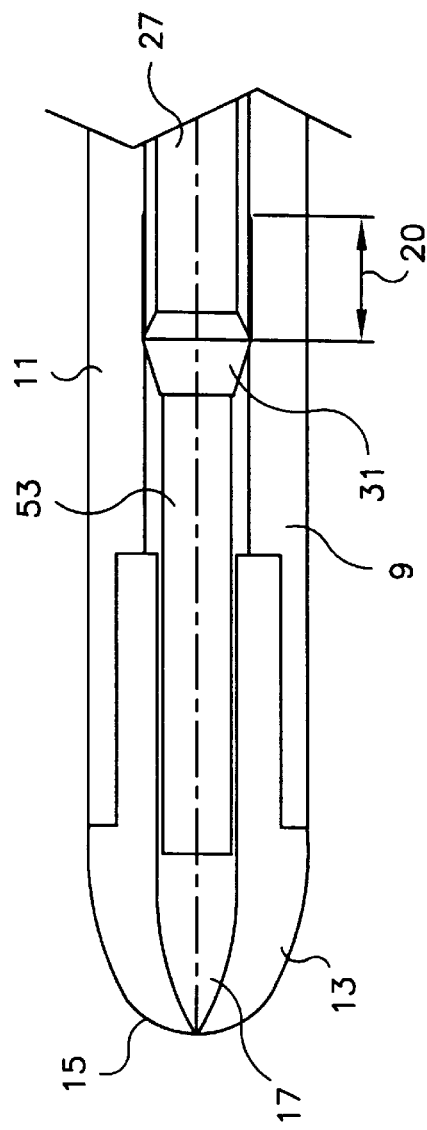
FIG. 3B is a bottom view of the retractor of FIG. 1.

Referring now to FIGS. 1, 2, and 3A there is shown a relatively rigid retractor formed of stiff rods 9, 11 that extend in substantially parallel spaced orientation to a distal end 13 that includes an upturned tip 15 and an underside channel or groove 17. The rods 9, 11 terminate at the proximal end via an upward bend 18 to rigid attachment to a connector block 19 that may, for example, include a longitudinal inverted "T"-shaped slot 21 therein. An elastic band 23 may be disposed near the distal end, for example, at the upward bend 18 to provide support near the proximal end for an endoscope support sheath, as later described herein. Of course other channeled or grooved configuration between proximal and distal ends of the retractor may also be used to provide rigidity, supporting space for an endoscope and detaching coupling to a handle at the proximal end.

Referring now to FIG. 3B, there is shown the underside of the elongated retractor with a protective and supportive sleeve or sheath 27 positioned, in the illustrated embodiment, substantially coplanarly with and between the rods 9, 11. An endoscope 53 is disposed within the protective sheath 27 and extends beyond the end of the sheath 27 to align within the underside groove 17 to a selected position in the tip 13 that provides adequate visualization during insertion of the retractor into a perivascular cavity. The sliding support 31 at the distal end of the sheath 27 may be configured to slide along the lengths of, and be retained by, the rods 9, 11 up to the cutout sections 20 of the rods 9, 11.

In another embodiment, the sliding support 31 is formed with sufficiently larger dimensions than the spacing between rods 9, 11 to prevent the distal end of the sheath 27 from passing between the rods 9, 11. The cutout sections 20 thus permit the sliding support 31 to disengage from the rods 9, 11 to enable the objective end of endoscope 53 to be positioned into the underside groove 17. As the endoscope 53 is advanced into the underside groove, the sliding support abuts the distal end of the cutout sections 20 to prevent further extension of the endoscope 53 into the tip 13. The cutout sections 20 thus allow the endoscope 53 to be positioned into the underside groove 17 in the tip 13 with the endoscope sheath or sleeve 27 in place, and also provide a stop for the endoscope 53. In operation, the sleeve 27 is attached to the endoscope 53 prior to placement of the retractor into a perivascular cavity. The endoscope 53 is retained in fixed longitudinal position within the sheath 27, as later described herein, and the forward extension of the endoscope 53 and sheath 27 is stopped by the sliding support 31 against the distal end of the cutout sections 20 rather than by the lens of the endoscope and a wall of the underside groove 17.

Figure 4:
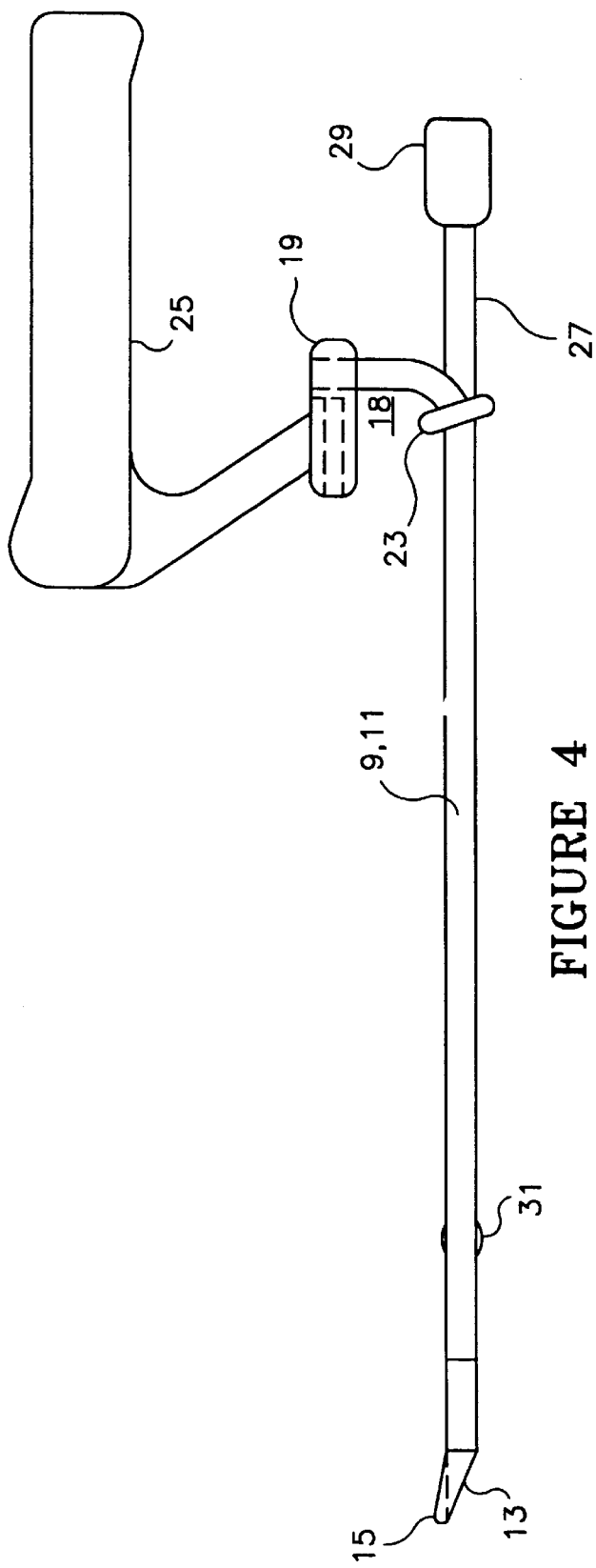
FIG. 4 is a side view of the retractor of FIG. 1 illustrating an attached handle.

Referring now to FIG. 4, there is shown the retractor of FIGS. 1, 2 and 3A including a handle 25 attached within the coupler 19, and the endoscope support sleeve 27 disposed along the channel or groove (i.e., spacing between spaced parallel rods 9, 11) substantially to the position of the distal tip 13. The sleeve or sheath 27 is a thin-wall rigid tube that includes at the proximal end a threaded endoscope coupling collar 29 for mating with and holding therein an endoscope with mating threaded proximal end, and includes at the distal end a sliding support 31. The sleeve or sheath 27 may be flexibly supported near its proximal end by the elastic band 23 positioned near and between the upturned section 18 of the rods, and may be supported at its distal end by the slidable support 31 within the channel between rods 9, 11. In this configuration, an endoscope disposed within the sleeve or sheath 27 may be supported thereby and may include an objective viewing end extended beyond the sheath 27, into the groove or channel on the lower side of the tip 13, substantially to a position near or beneath the upturned tip 15. Thus configured, the retractor with attached handle 25 and endoscope (not shown) within the sleeve or sheath 27 may be manually inserted into a perivascular cavity formed along the target vessel to be harvested, substantially to the entire length thereof to the upturned region 18. Then, the handle 25 may be conveniently detached from the coupler 19 for attachment to the elevator of the retractor frame, as shown in FIGS. 5, 6, and 7.

Referring to these figures, there is illustrated one embodiment of a supporting frame including a base formed of stiff rod 33 in a looped configuration, and a yoke 35 to retain the sides of the base formed by rod 33 in substantially parallel orientation. The distal end of the base may include upturned end loop 37, and the proximal end of the base may include the ends 39, 41 of the looped rod 33 bent in divergent pattern but in substantially planar configuration. A mating T-shaped receptor 43 is configured to facilitate sliding attachment to the T-shaped slot in the coupler 19 of the retractor of FIGS. 1, 2, 3A, and is disposed on a ratcheted, manually-adjustable vertical post 45. A T-shaped handle (or other conveniently-grippable knob) 47 on the upper end of the post 45 enables the surgeon to elevate the post 45 and attached retractor, assembled as illustrated in FIGS. 8, 9 and 10, to an extent that expands or distends a perivascular cavity 49 by elevating the adjacent skin and tissue 51, as illustrated in the end view of FIG. 9. In this way, the surgeon can retain tactile control on the extent or degree of stretching of skin and tissue 51, thereby to minimize vascular damage and possible skin necrosis. The base of the retractor frame 33 is positioned on the patient in proximity, and substantially along the course, of the target vessel.

Figure 11:
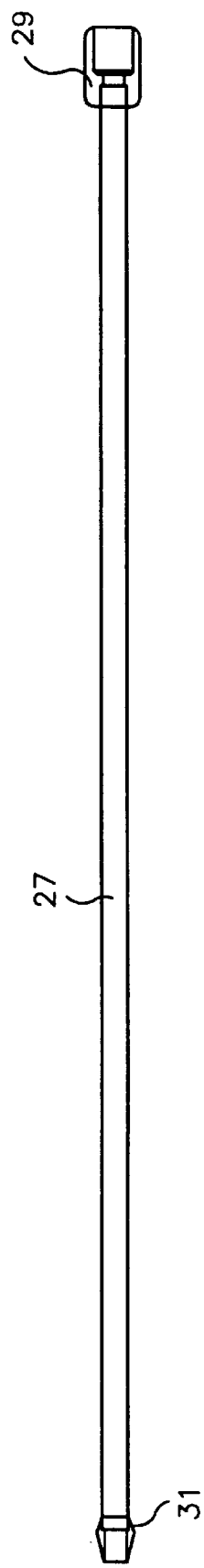
FIG. 11 is a side view of an endoscope support sleeve for longitudinally slidable engagement with and support by the retractor.

Following elevation of the retractor 9, 11, the endoscope (which provided visualization during insertion of the tip 13, 15 into the perivascular cavity) may be withdrawn. The slidable support 31 at the distal end of the supporting sleeve or sheath 27 may engage the two rods 9, 11 for support therebetween to support the distal end during withdrawal, while the elastic band 23 supports the sleeve or sheath 27 near the proximal end during withdrawal of the sleeve or sheath 27 and the contained endoscope. The sleeve or sheath 27, as illustrated in FIG. 11, is thus slidably mounted in the space between rods 9, 11 (or within other channel or groove configuration), with the distal end thereof supported by the sliding support 31 for convenient sliding placement and withdrawal of the sleeve 27 and enclosed endoscope.

Figure 12:
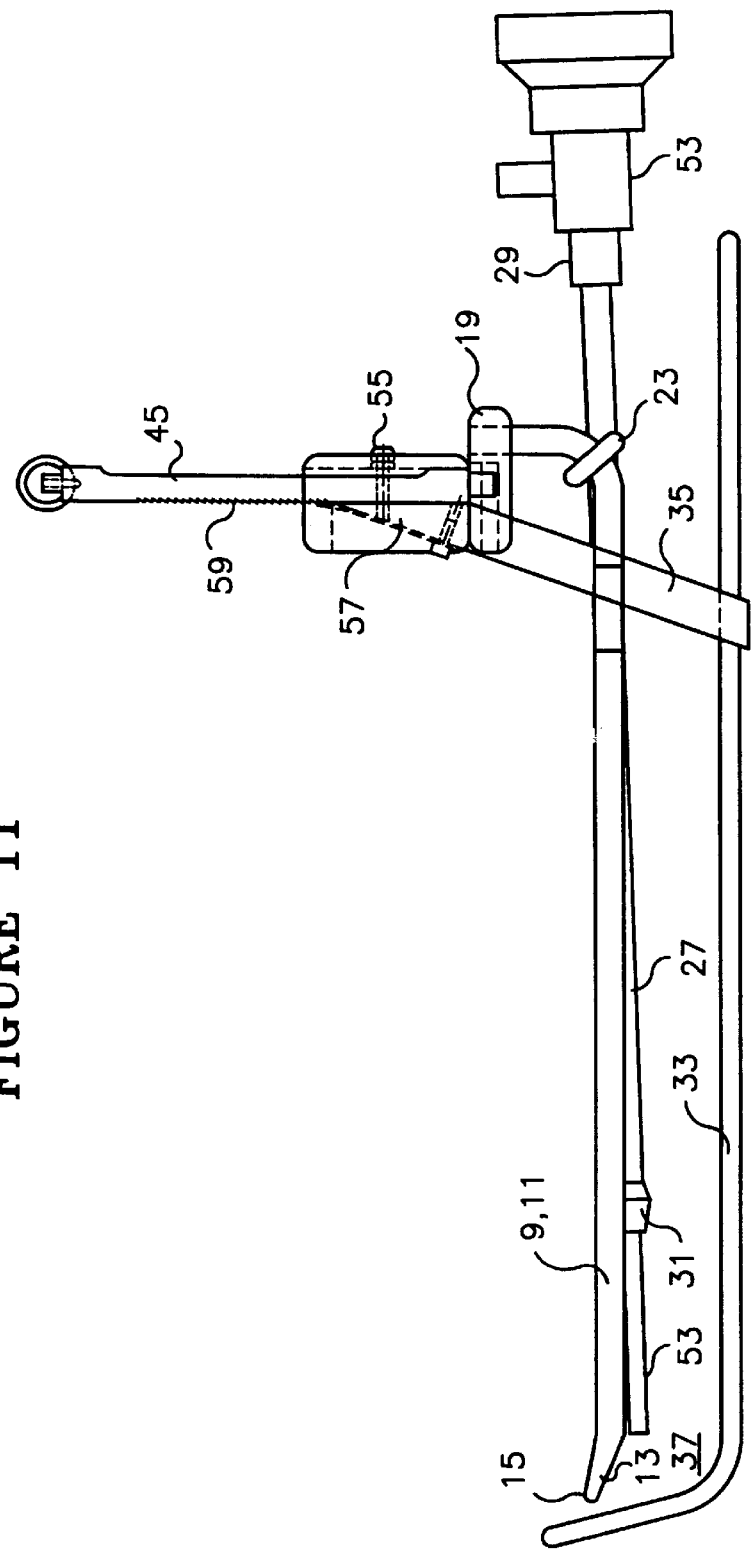
FIG. 12 is a side view of the assembly of FIG. 8 including an endoscope and support sleeve disposed on the retractor of FIG. 1.

Referring now to FIG. 12, there is shown a side view of the assembled retractor, with endoscope 53 and retractor frame, shown at elevated position on the ratcheted vertical post 45. Of course, the endoscope 53 may include an imaging camera of conventional construction mounted at the location of the eyepiece for tradition television imaging of the operating site within the field of view of the endoscope. The elevational setting of the retractor relative to the rod 33 that forms the base of the retractor frame may be lowered against ratcheted stops by depressing release button 55 that disengages the ratcheting spring 57 from the ratchet stops 59 along the vertical post 45.

Therefore, the retractor and associated assemblies and procedures described herein greatly facilitate manually-controlled insertion (under endoscopic visualization) and elevation of a retractor within a perivascular cavity for maximum exposure and access to tissue therein. The parallel rods which comprise the elongated loop lifts a planar section of the cavity, but allows access to all tissue not in contact with the rods. In this way, a surgeon may form a distended or expanded perivascular cavity along the length of a vessel of interest (such as the saphenous vein), and may then proceed to dissect the vessel from connective tissue, occlude lateral or branch vessels, or otherwise perform tissue manipulations to harvest the vessel of interest in known manner within the ample space provided within the distended perivascular cavity by the elevated retractor and retractor frame assembly. Thereafter, the retractor may be released from the elevated position by releasing the ratcheted vertical post, and may then be withdrawn from the perivascular cavity, and the retractor frame can be removed from its position of the skin of the patient.

The combination of the sleeve or sheath with a sliding support tip at the distal end thereof, and with an elastic band near the proximal end of the retractor allows the endoscope to move along the cavity with the retractor while being maintained in the correct orientation to visualize the main bore of the perivascular cavity. The retractor may remain stationary and support the cavity while the position of the endoscope may be adjusted along the length of the cavity.

The coupling or connector block between the elongated retractor, the removable handle, and the retractor frame allows careful placement of the elongated retractor in the subcutaneous space under direct vision, without injury to the vessel of interest. The retractor frame can be added after placement of the retractor. The retractor frame may be positioned and the retractor may be elevated without disturbing the longitudinal position of the retractor, thereby avoiding shear forces against the vessel and surrounding tissue that may cause injury.

The ratchet lock system on the vertical post allows the operator to easily lift the ceiling of the cavity, and gauge the amount of force exerted on the skin. Excessive stretching which may cause devascularization of the skin, leading to skin necrosis, is avoided by relying upon direct mechanical lifting rather than upon a screw type of lift that can contribute increased mechanical advantage to elevate the ceiling of the perivascular cavity with concomitant increased possibility of injury to the skin due to excessive stretching under screw-magnified applied force.

What is claimed is:

1. Apparatus for distending a perivascular cavity at a surgical site on a patient, the apparatus comprising:

an elongated retractor including a channel member extending from a proximal end to a distal end, and including a tip attached at the distal end;

a coupler attached to the retractor near the proximal end thereof for selectively forming mechanical connection to the retractor; and a retractor frame including a base positionable on the skin of the patient about a surgical site and including an elevator element supported with respect to the base for selective adjustment of the elevator element substantially vertically relative to the base and supporting on the elevator element a mating coupling for selective attachment of the retractor thereto.

2. Apparatus according to claim 1 wherein said tip includes an upper side and an underside in relation to the direction of elevation of the retractor by the elevator element of the retractor frame, and the upper side of the tip is upturned at the distal end thereof.

3. Apparatus for distending a perivascular cavity at a surgical site on a patient, the apparatus comprising:

an elongated retractor including a channel member extending from a proximal end to a distal end, and including a tip attached at the distal end, said retractor includes a pair of stiff rods disposed in substantially parallel spaced orientation over a portion of the length thereof between distal and proximal ends of the retractor, and includes a sheath slidably supported on the retractor for supporting an endoscope therein substantially to the distal end of the tip;

a coupler attached to the retractor near the proximal end thereof for selectively forming mechanical connection to the retractor; and a retractor frame including a base positionable about a surgical site and including a selectively adjustable elevator element supported with respect to the base and supporting thereon a mating coupling for selective attachment of the retractor thereto.

4. Apparatus according to claim 3 wherein said tip includes an elongated groove disposed on the underside of the tip substantially in alignment with the sheath to receive an endoscope longitudinally positionable therein with respect to the distal end of the tip.

5. Apparatus for distending a perivascular cavity at a surgical site on a patient, the apparatus comprising:

an elongated retractor including a channel member extending from a proximal end to a distal end, and including a tip attached at the distal end;

a coupled attached to the retractor near the proximal end thereof for selectively forming mechanical connection to the retractor;

a retractor frame including a base positionable about a surgical site and including a selectively adjustable elevator element supported with respect to the base and supporting thereon a mating coupling for selective attachment of the retractor thereto, said elevator element being supported in the retractor frame for substantially vertical movement relative to the base, and including ratchet settings of vertical elevation for retaining an elevational position relative to the base; and a ratchet release positioned in the retractor frame to selectively release a ratchet setting of elevational position relative to the base.

6. A method for manipulating a perivascular cavity in a patient with an elongated retractor and retractor frame, the method comprising the steps of:

assembling an endoscope longitudinally along the length of the retractor substantially to the distal end thereof to provide visualization of tissue during insertion of the retractor into the cavity;

inserting the retractor into the perivascular cavity substantially to the length of the retractor between a distal end and a proximal end thereof;

positioning the retractor frame of substantially similar length as the retractor to bear upon the skin of the patient in substantial alignment with, and on opposite sides of, the retractor disposed within and along the perivascular cavity;

attaching the retractor near the proximal end thereof to the retractor frame and selectively elevating the retractor to form a distended perivascular cavity including the skin of the patient stretched between the elevated retractor and the retractor frame bearing upon the skin of the patient.

7. The method according to claim 1 wherein the retractor includes a tip at the distal end thereof to facilitate insertion into a perivascular cavity, and the endoscope is disposed below the tip to provide visualization within the perivascular cavity substantially below the retractor.

8. The method according to claim 1 comprising the step of:

slidably removing the endoscope from the retractor following insertion thereof into the perivascular cavity.

9. The method according to claim 1 wherein the step of selectively elevating the retractor includes locking the retractor at selected elevated position to retain the perivascular cavity in distended condition, and thereafter selectively releasing the retractor from locked elevational position following manipulations within the distended perivascular cavity.

* * * * *